(12) United States Patent
Kaneblei et al.

(10) Patent No.: US 8,262,999 B2
(45) Date of Patent: Sep. 11, 2012

(54) PROCESS FOR PUTTING INTO OPERATION AND FOR OPERATING A MEASURING DEVICE

(75) Inventors: Ingo Kaneblei, Herrnburg (DE); Thomas Wuske, Malente (DE); Rainer Polzius, Lübeck (DE); Björn Lange, Teschow (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 541 days.

(21) Appl. No.: 12/390,715

(22) Filed: Feb. 23, 2009

(65) Prior Publication Data
US 2009/0249894 A1 Oct. 8, 2009

(30) Foreign Application Priority Data
Apr. 4, 2008 (DE) .......................... 10 2008 017 196

(51) Int. Cl.
*G01N 21/00* (2006.01)

(52) U.S. Cl. ...... 422/82.05; 422/67; 422/68.1; 436/174; 436/176

(58) Field of Classification Search ............ 422/63, 422/65, 67, 68.1, 82.05, 82.09, 82.12, 400, 422/402, 403, 408, 430, 501, 509, 529, 530; 436/43, 44, 46, 47, 164, 165, 169, 518, 809, 436/174, 176; 435/4, 7.1, 7.4; D24/216, D24/223, 224, 227; 73/863, 863.91, 864.91; 702/22, 127; 356/244
See application file for complete search history.

(56) References Cited

U.S. PATENT DOCUMENTS

| 5,038,852 | A | * | 8/1991 | Johnson et al. ............... 165/267 |
| 5,039,492 | A | * | 8/1991 | Saaski et al. ............... 422/82.09 |
| 5,236,666 | A | | 8/1993 | Hulette |
| 5,374,395 | A | * | 12/1994 | Robinson et al. ............... 422/64 |
| 5,405,510 | A | * | 4/1995 | Betts et al. ..................... 205/782 |
| 5,580,794 | A | | 12/1996 | Allen |
| 5,635,364 | A | * | 6/1997 | Clark et al. .................. 435/7.92 |
| 5,851,488 | A | * | 12/1998 | Saul et al. ........................ 422/67 |
| 6,958,129 | B2 | * | 10/2005 | Galen et al. .................. 422/400 |
| 7,070,920 | B2 | | 7/2006 | Spivey et al. |
| 2001/0034068 | A1 | | 10/2001 | Spivey et al. |
| 2002/0127708 | A1 | * | 9/2002 | Kluttz et al. ............... 435/287.2 |
| 2006/0105359 | A1 | * | 5/2006 | Favuzzi et al. .................... 435/6 |
| 2009/0053814 | A1 | * | 2/2009 | Patel et al. ......................... 436/8 |

(Continued)

FOREIGN PATENT DOCUMENTS
CA 2243801 5/1999
(Continued)

*Primary Examiner* — Jill Warden
*Assistant Examiner* — Dwayne K Handy
(74) *Attorney, Agent, or Firm* — McGlew and Tuttle, P.C.

(57) ABSTRACT

Tempering of sample (58) in test strip (37) is carried out by temperature regulating unit (40) and heating/cooling unit (92). The sample is fed to the test strip by a developer fluid (57) and a metering unit (55). The result of the detection reaction becomes visible by a change in color (36), which is detected optically and analyzed. The data of a control chart (52) with the measured values of first and second temperature sensors (41, 42) are used to set the control parameters for tempering. Code (86) on the test sample holder (35) is read in a sequence of steps. Parameters for phases of the measurement are determined from measured values of first and second temperature sensors, values of the control chart and the code of the test sample holder. These parameters are used by the temperature regulating unit during the measurement.

32 Claims, 5 Drawing Sheets

U.S. PATENT DOCUMENTS

2009/0068062 A1 * 3/2009 Jafari et al. .................. 422/64

FOREIGN PATENT DOCUMENTS

| | | |
|---|---|---|
| DE | 195 46 535 A1 | 6/1997 |
| DE | 197 51 363 A1 | 6/1999 |
| DE | 695 11 533 T2 | 4/2000 |
| DE | 101 33 996 A1 | 9/2002 |
| DE | 699 15 481 T2 | 3/2005 |
| DE | 10 2004 062 25 | 2/2006 |
| EP | 1 736 772 A1 | 12/2006 |
| GB | 24 58 777 A | 10/2009 |

* cited by examiner

|  | Phase 1 | | Phase 2 | |
|---|---|---|---|---|
|  | Temp 1 | Intervall 1 | Temp 2 | Intervall 2 |
| <0°C |  |  |  |  |
| 0..5°C |  |  |  |  |
| 5..10°C |  |  |  |  |
| 10...15°C |  |  |  |  |
| 15..20°C |  |  |  |  |
| 20...25°C |  |  |  |  |
| 25°C...30°C |  |  |  |  |
| 30°C 35°C |  |  |  |  |
| 35°C 40°C |  |  |  |  |
| 40°C 45°C |  |  |  |  |
| >45°C |  |  |  |  |

FIGURE 3

PROCESS FOR PUTTING INTO OPERATION AND FOR OPERATING A MEASURING DEVICE

CROSS REFERENCE TO RELATED APPLICATIONS

This application claims the benefit of priority under 35 U.S.C. §119 of German Patent Application DE 10 2008 017 196.4 filed Apr. 4, 2008, the entire contents of which are incorporated herein by reference.

FIELD OF THE INVENTION

The present invention pertains to a measuring device for the analysis of biological material and to a process for putting into operation and for operating the measuring device.

BACKGROUND OF THE INVENTION

A device for the analysis of biological material, in which a test sample holder is inserted into a measuring device, is known from DE 69915481 T2. The analysis of biological material, for example, human saliva, is described in DE 19751363 B3. It is necessary here, in a sequence of process steps, to collect a sample of the biological material in a suitable tank, to meter a defined quantity of an aqueous developer solution, and to insert the mixture of aqueous solution and biological material into a test sample holder, into which a test strip is placed. The test strip contains a collection matrix and a detection matrix. The presence or absence of an analyte in the collected biological material is demonstrated by an immunochemical detection reaction. The presence of the analyte to be detected in the sample of the biological material causes a color change on the test strip in the detection reaction.

The device known from DE 69915481 T2 uses an optical analysis unit for the analysis of the color change. A combination of immunochemical detection reaction and chromatographic analysis is thus obtained. The course of the immunochemical reaction depends essentially on the processing times and ambient conditions, the rate of the reaction process and hence the reproducibility of the detection of an analyte in a sample of biological material being affected especially by the temperature.

A test sample holder for collecting a quantity of biological material is known from DE 19546565 A1, and another embodiment of a test sample holder is known from US 20010034068 A1.

Parts of the analytical process step, e.g., the collection of the sampler and the metering with the developing fluid onto the sample take place outside the device in the device specified in DE 69915481 T2. It is disadvantageous in such an embodiment that the effects of the ambient conditions, especially of the temperature, cannot be controlled for the duration of the detection reaction. This limits the temperature range in which the measuring device can be used without affecting the reproducibility.

Furthermore, it is disadvantageous that the time period between the metering of the developer fluid onto the sample and the chromatographic analysis continues to be at the discretion of the user and thus also affects the subsequent measurement. The consequence of this is a fluctuation of the measurement results due to the process and, as a result, a greater measuring uncertainty over the entire measuring chain.

SUMMARY OF THE INVENTION

An object of the present invention is therefore to propose a measuring device and a process for actuating same in such a way that the reproducibility of the measurement process is improved and the effect of the ambient conditions is reduced.

According to the invention, a measuring device is provided with an electronic unit comprising a central control unit, a sequential control and a control chart. An optical analysis unit is provided with an optical reading element. A metering unit, a holder for a fluid tank containing a developer fluid, a temperature regulating unit and a heating/cooling element for generating a tempered zone of a test sample holder are also provided. First and second temperature sensors are provided for detecting the ambient temperature and the temperature of the tempering block. At least one contact means is provided for controlling the measuring operation.

The advantage of the present invention is essentially that all processing steps of the detection reaction take place in the interior of the measuring device and no preparatory preparation of the sample with a developer fluid by the user must be performed outside the measuring device.

The process according to the present invention for putting into operation and for operating a measuring device is characterized by a sequence of the following steps such that:
a) In a first step, a section of the process control is transferred by the central control unit to the process control and to the temperature regulating unit,
b) in a second step, the first and second temperature sensors are polled and the temperature regulating unit is prepared,
c) the test sample holder is inserted into the measuring device in a third step,
d) the fluid tank with the developer fluid is inserted into the holder in a fourth step,
e) the door of the device is closed in a fifth step,
f) the at least first contact element is polled in a sixth step,
g) the at least second contact element is polled in a seventh step,
h) the at least third contact element is polled in an eighth step,
I) the code on the test sample holder is polled in a ninth step,
j) the control chart, code and measured values of the first and second temperature sensors are used to determine the control parameters for the tempering in a tenth step,
k) tempering of the tempering block is brought about in an eleventh step and the temperature of the tempering block is regulated by the temperature regulating unit,
l) the metering of the developer fluid onto the sample is brought about by means of the metering unit in a twelfth step,
m) tempering of the tempering block is brought about and the temperature of the tempering block is regulated by the temperature regulating unit in a thirteenth step,
n) tempering is ended in a fourteenth step, and
o) the process control is again taken over by the central control unit in a fifteenth step.

Provisions are made in a special embodiment of the process for the insertion of the fluid tank provided in the third step to be omitted and for feeding a defined quantity of developer fluid from a storage tank in the interior space of the measuring device into a metering tank to be brought about, instead.

In an alternative course of the process, pretempering of the tempering block is performed already in the second step, which makes possible a short time for establishing the readiness to operate after starting up the device. This is a meaningful variant when, for example, the measuring device is operated with an external supply voltage and the operating time is not shortened in a disadvantageous manner as a consequence of the energy consumption by a continual tempering.

The analysis taking place in the measuring device is started in the manner according to the present invention by a sequential control by means of a switching means.

This switching means may be a button actuated by the user, which is arranged on the operating unit of the measuring device. This button is, for example, part of a unit for operating and outputting user instructions and measured values and is labeled "START." As an alternative, a switching contact is present as an additional switching means, which detects the insertion of the test sample holder into the interior space of the measuring device. The opening or closing of a door of the device after insertion of the test sample holder can be detected by means of other switching means in an alternative embodiment, and the insertion of the fluid tank with the developer fluid into a holder can be additionally detected in another preferred embodiment.

The test sample holder is provided with a code, which can be detected by means of optical reading and subsequently analyzed. Mechanical switches, magnetically actuated switches and a device in the form of a photoelectric cell are conceivable as switching means in respective alternative embodiments.

The switching means and the code of the test sample holder are polled after the insertion of the test sample holder into the measuring device and of the fluid tank with the developer fluid into the holder, and the first phase of measurement will subsequently begin.

The phases of the measurement with tempering of the test sample holder are given by preset time intervals of a defined duration with at least one preset first tempering temperature. The tempering of the test sample holder brings about indirectly a tempering of the test strip via a tempering block. The tempering block is brought to the first tempering temperature at the beginning, the developer fluid is metered onto the sample in the next step, and the mixture of developer fluid and sample of the biological material is tempered indirectly in the test strip in a next step according to a preset, second tempering temperature. The tempering temperature is detected by a first temperature sensor, which is rigidly connected to the tempering block with a good temperature coupling. To determine the ambient conditions, a second temperature sensor, which has a design suitable for detecting the air temperature in the interior space of the measuring device, is arranged in the interior space of the measuring device. The fluid tank with the developer fluid is not placed by the user into the holder during each analysis operation in an alternative embodiment, but a quantity of developer fluid is made available for the metering unit from an internal storage tank of the device. The tempering block is made of a metallic material in a preferred embodiment.

The duration of the phases of measurement for tempering and metering, as well as the first and second tempering temperatures are determined on the basis of the ambient conditions, the codes of the test sample holder, as well as preset data of a control chart.

At least one control chart, which contains the tabular values for the tempering temperatures and the time intervals of the phases of measurement, is present for this in a data storage unit.

The values for the tempering temperatures and the time intervals for tempering and metering have been determined empirically on the basis of measuring experiments for different detection reactions. Different codes are preferably placed on the test sample holders for different detection reactions, and the specific control chart can be identified on the basis of these codes and used to determine the specific tempering parameters. A subsequent refreshing and complementation of the control chart by means of data transmission via a data interface is provided in an advantageous embodiment in order to make it possible to adapt the process parameters of the measuring device to the further development of the biological analytical procedures.

The temperature of the heating element is regulated with the use of the tabular values in the data storage medium, the code of the test sample holder and the measured signals of the first and second temperature sensors, and regulation is preferably performed according to a proportional-integral control characteristic. The tempering of the tempering block is carried out by means of a heating element and a cooling element, and a combination of heating function and cooling function can be selected in a special embodiment by the use of a Peltier element. The opposite side of the Peltier element is coupled here by a cooling body to the ambient air.

A special embodiment contains, in addition to the heating/cooling element designed as a Peltier element, an additional element, which may be designed, for example, as an electric resistance heating element or as a semiconductor heating element in the form of a transistor, in order to shorten the heat-up time of the tempering block.

An additional energy storage unit with low internal resistance, preferably a rechargeable battery, which can supply the electric current necessary for a rapid temperature change in a short time, is provided in an advantageous embodiment to shorten the measuring time. Pretempering of the tempering block may also be carried out already before the insertion of the test sample holder in an advantageous embodiment.

This is a meaningful variant when, for example, the measuring device is operated by means of an external supply voltage and therefore the operating time is not shortened as a consequence of discharge of the battery due to continual tempering.

An exemplary embodiment of the present invention is shown in the drawings and will be explained in more detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 3 shows the exemplary design of a control chart;

DESCRIPTION OF THE PREFERRED EMBODIMENTS

Figure 1:
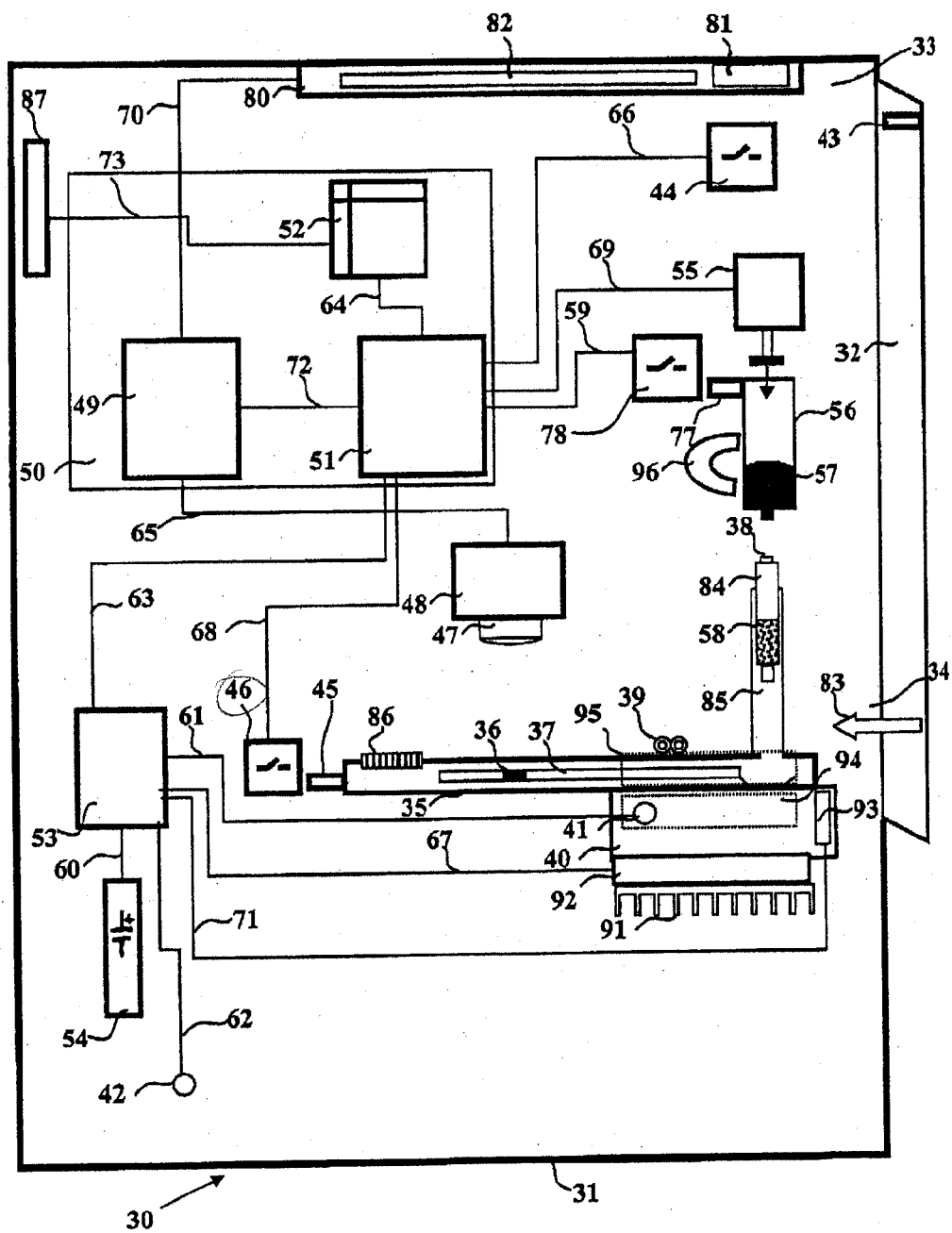
FIG. 1 is a schematic view showing the design of a measuring device for the analysis of a sample of biological material.

Referring to the drawings in particular, FIG. 1 schematically shows a measuring device 30 for the analysis of saliva samples, in which a test sample holder 35 is inserted into the interior space 33 via an access opening 34.

A collector tube 85, which contains a collector element 84 with a sample 58 of the analyte, is arranged at the test sample holder 35. This measuring device 30 comprises a housing 31 with an operating and output unit 80, with an electronic unit 50, which is divided into the components central control unit 49, sequential control 51 and a data storage unit with a control chart 52; a metering unit 48 with an optical reading element 47; a metering unit 55, and a temperature regulating unit 53.

The line connections of the individual components are shown in FIG. 1, partly with a crossed line routing, and will now be specifically described.

The sequential control 51 is connected to a control chart 52 via a first data line 64, to a first contact element 44 via a first contact line 66, to a second contact element 46 via a second contact line 68, to a third contact element 78 via a third contact line 59, and to the temperature regulating unit 53 via a first control line 63.

The central control unit 49 is connected to the optical analysis unit 48 via a second data line 65 and to the operating and analysis unit 80 via a third data line 70 and to the sequential control 51 via a fourth data line 72.

A fifth data line 73 connects the control chart 52 to a data interface 87.

The control chart 52 according to FIG. 3 contains a first set of temperature values 103 and time period values 104 and a second set of temperature values 105 and time period values 106.

The temperature regulating unit 53 is connected to a first temperature sensor 41 via a first measuring line 61 and to a second temperature sensor 42 via a second measuring line 62.

Via a second control line 67, the temperature regulating unit 53 is connected to the heating and cooling elements, in this case in one embodiment as a combined heating/cooling element 92 in the form of a Peltier element. An additional heating element 93 is connected to the temperature regulating unit 53 via a fourth control line 71. The temperature regulating unit 53 is connected to an energy storage unit 54 via a supply line 60. The heating/cooling element 92 is attached to the tempering block 40 on one side and is provided on the other side with a cooling body 91, via the surface of which good thermal coupling with the ambient temperature is ensured. The sequential control 51 is connected to a metering unit 55 via a third control line 69.

The sample 58 in the test sample holder 35 and the test strip 36, which is located on the test sample holder 35, are inserted into the interior space 33 of housing 31 from the direction of access 83 via a push-in guide 39. The fluid tank 56 with the developer fluid 57 is inserted into the interior space 33 and placed into the holder 96. The access opening 34 is closed by a door 32 of the device after insertion of the test sample holder 35 and the insertion of the fluid tank 56, and the interior space 33 is thus separated from ambient effects. The closing of the door 32 of the device is detected via the first contact element 44, which is actuated by a first contact maker 43 located on the door 32 of the device. The position of the test sample holder 32 is detected by the second contact element 46, which is actuated by a second contact maker 45, which is arranged on the test sample holder 35 or is formed by the test sample holder 35 itself. The position of the fluid tank 56 is detected by the third contact element 78, which is actuated by a third contact maker 77, which is arranged on the fluid tank 56 or is formed by the fluid tank 56 itself. The metering unit 55 brings about the dispensing of a developer fluid 57 from a fluid tank 56 via the access opening 38 through the collector element 84 containing the sample 58 in the collector tube 85 onto an array of test strips 37 in the test sample holder 35.

The course of the process according to the present invention is as follows: After a start button 81 and the first, second and third contact elements 44, 46, 78 have been polled and after a code 86 has been detected on the test sample holder 35 by the optical reading element 47 and after the code 86 has been analyzed by the optical analysis unit 48, and after the subsequent detection of the first and second temperature sensors 41, 42, the central control unit presets the temperature of the tempering zone 94 of the tempering block 40 (and the block tempering zone 94), which said temperature is to be controlled, for the temperature regulating unit 53 on the basis of the control chart 52.

The tempering of the tempering zone 94 in the tempering block 40 brings about a tempering of the tempering zone 95 in the test sample holder 35. The temperature regulating unit 53 actuates the heating/cooling element 92 and the additional heating element 93 and regulates the tempering zone 94 in tempering block 40 according to the control characteristics set, for example, according to a proportional-integral (PI) control characteristic. The first and second phases of the measurement and the metering of the developer fluid 57 onto the test strip 37 are controlled according to the contents of the control chart 52.

The tempering temperatures for the first and second phases are determined by the code of the test sample holder 35 and by the data contents 103, 105 of the control chart 52; the overall duration of measurement is determined by the data contents 104, and the duration of metering for the developer fluid 57 onto the test strip 37 is determined by the data contents 106 of the control chart 52. After the end of the first phase, the developer fluid 57 is metered by means of the metering unit 55, and the temperature is regulated to the second temperature during the second phase.

After the end of the second phase, the change in color 36 on the test strip 37 is detected via the optical reading element 47, analyzed in the optical analysis unit 48, transmitted to the central control unit 49, and displayed on a display 82 of the operating and output unit 80.

Figure 2:
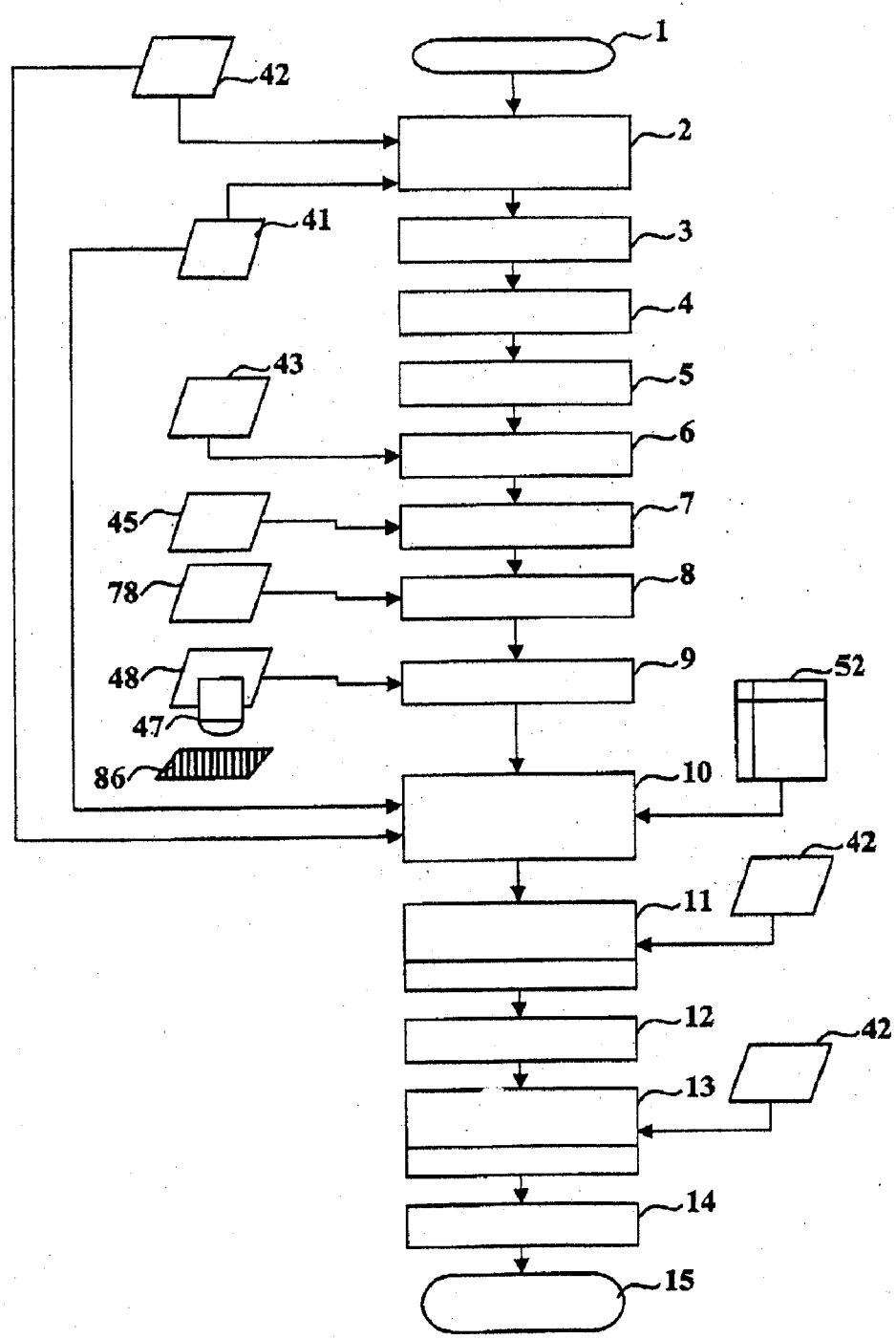
FIG. 2 is a schematic view showing the course of the putting into operation and tempering of the measuring device.
Figure 4:
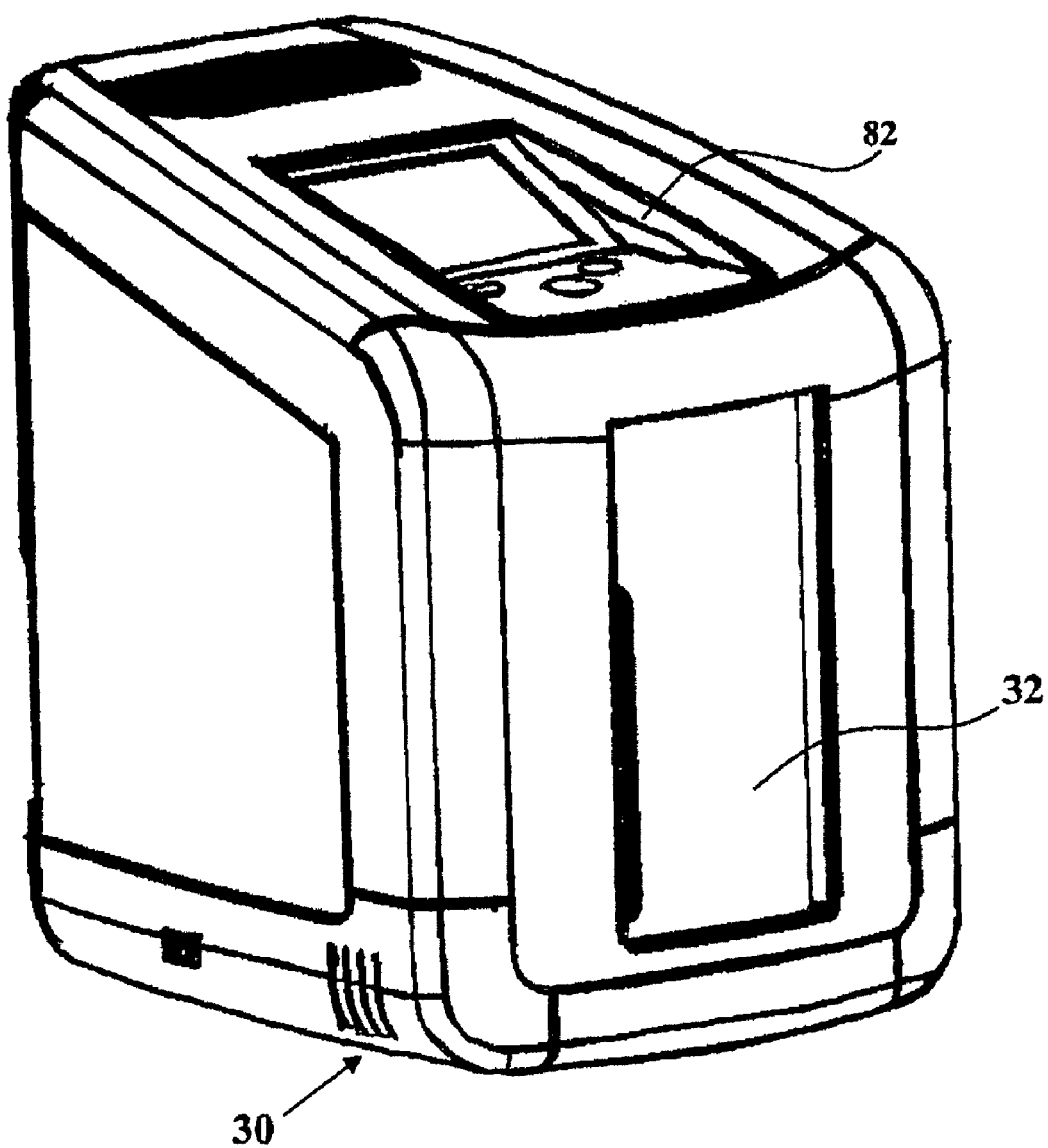
FIG. 4 is an external view of the measuring device for the analysis of a sample of biological material.
Figure 5:
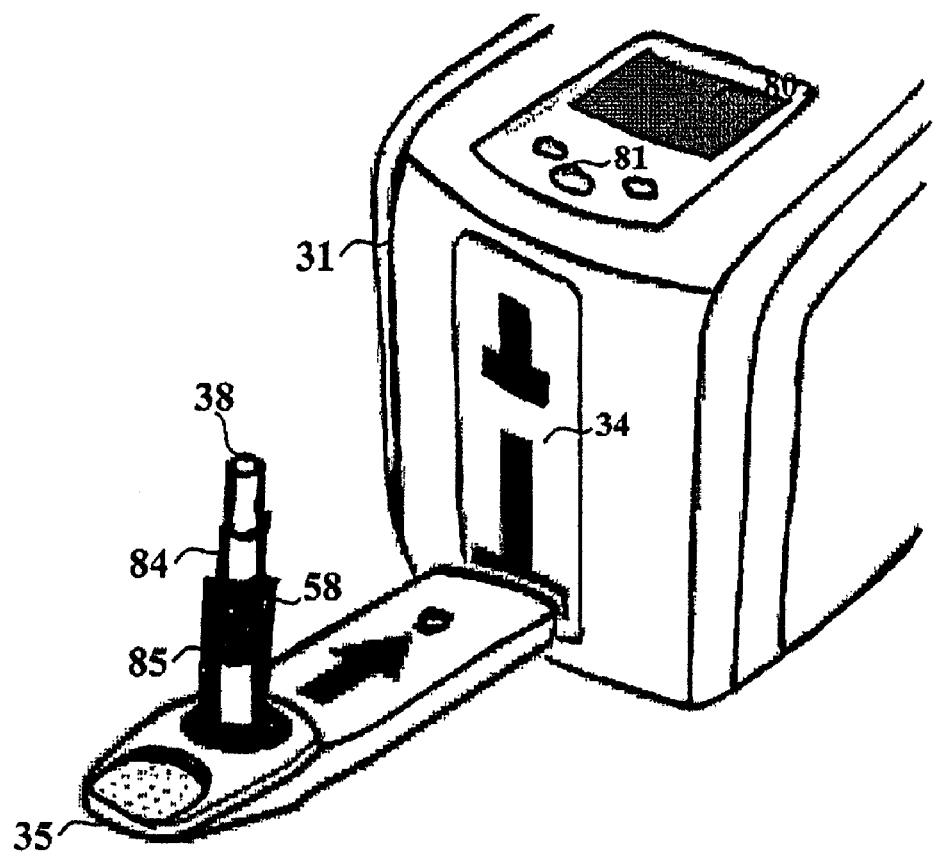
FIG. 5 is an external view of the measuring device in connection with the test sample holder and the insertion thereof into the measuring device.

The process according to the present invention for putting into operation and for operating the measuring device is shown in FIG. 2 and is characterized by a sequence of the following steps such that:

a) In a first step 1, a section of the process control is transferred by the central control unit to the process control and to the temperature regulating unit, b) in a second step 2, the first and second temperature sensors are polled and the temperature regulating unit is prepared, c) the test sample holder is inserted into the measuring device in a third step 3, d) the fluid tank with the developer fluid is inserted into the holder in a fourth step 4, e) the door of the device is closed in a fifth step 5, f) the at least first contact element is polled in a sixth step 6, g) the at least second contact element is polled in a seventh step 7, h) the at least third contact element is polled in an eighth step 8, I) the code on the test sample holder is polled in a ninth step 9, j) the control chart, code and measured values of the first and second temperature sensors are used to determine the control parameters for the tempering in a tenth step 10, k) tempering of the tempering block is brought about in an eleventh step 11 and the temperature of the tempering block is regulated by the temperature regulating unit, l) the metering of the developer fluid onto the sample is brought about by means of the metering unit in a twelfth step 12,
m) additional and different tempering of the tempering block is again brought about, and the temperature of the tempering block is regulated by the temperature regulating unit in a thirteenth step 13,
n) tempering is ended in a fourteenth step 14, and
o) the process control is again taken over by the central control unit in a fifteenth step 15.

FIG. 3 shows the structure of the control chart 52. The chart is divided into a specification column 100, in which the values of the ambient temperature are entered as a reference variable, and a first value block 101 and a second value block 102. The time period values 104 for the overall duration of the measurement are entered in value block 101. The temperature values 103 are entered there for the first phase of the measurement. The temperature values 105 for the second phase of the measurement and the time period values 106 for metering the developer fluid 57 onto the test strip 37 located in the test sample holder 35 are entered in a second value block 102.

While specific embodiments of the invention have been shown and described in detail to illustrate the application of the principles of the invention, it will be understood that the invention may be embodied otherwise without departing from such principles.

Appendix
List of Reference Numbers
1 Step 1, transfer of control from the central control unit
2 Step 2, initialization, polling of the temperature sensors
3 Step 3, insertion of the test sample holder
4 Step 4, insertion of the fluid tank
5 Step 5, closing of the device door
6 Step 6, polling of the first contact element
7 Step 7, polling of the second contact element
8 Step 8, polling of the third contact element
9 Step 9, reading of the code
10 Step 10, determination of the control parameters
11 Step 11, tempering
12 Step 12, metering
13 Step 13, tempering
14 Step 14, ending of measurement
15 Step 15, return of control to the central control unit
30 Measuring device
31 Housing
32 Device door
33 Interior space
34 Access opening
35 Test sample holder
36 Color change marking
37 Test strip
38 Access opening
39 Push-in guide
40 Tempering block
41 First temperature sensor
42 Second temperature sensor
43 First contact maker
44 First contact element
45 Second contact maker
46 Second contact element
47 Optical reading element
48 Optical analysis unit
49 Central control unit
50 Electronic unit
51 Sequential control
52 Control chart
53 Temperature regulating unit
54 Energy storage unit
55 Metering unit
56 Fluid tank
57 Developer fluid
58 Sample
59 Third contact line
60 Supply line
61 First measuring line
62 Second measuring line
63 First control line
64 First data line
65 Second data line
66 First contact line
67 Second control line
68 Second contact line
69 Third control line
70 Third data line
71 Fourth control line
72 Fourth data line
73 Fifth data line
77 Third contact maker
78 Third contact element
80 Operating and output unit
81 Button (start)
82 Display
83 Direction of access
84 Collector element
85 Collector tube
86 Code
87 Data interface
91 Cooling body
92 Heating/cooling element
93 Additional heating element
94 Tempering zone, block
95 Tempering zone, test sample
96 Holder
100 Specification column
101 First value block
102 Second value block
103 First set of temperature values
104 First set of time period values
105 Second set of temperature values
106 Second set of time period values

What is claimed is:
1. A measuring device comprising:
an electronic unit including a central control unit, a sequential control and a control chart;
an optical analysis unit with an optical reading element;
a metering unit;
a fluid tank containing a developer fluid;
a holder for said fluid tank;
a temperature regulating unit;
a test sample holder;
a heating/cooling element with a tempering block for generating a tempered zone of the test sample holder;
a first temperature sensor;
a second temperature sensor, said first temperature sensor and said second temperature sensor being provided for detecting an ambient temperature and a temperature of the tempering block respectively, said central control unit selectively setting a temperature of said tempering block based on the ambient temperature and information from said control chart, said control unit controlling a set temperature of said tempering block using said second temperature sensor; and
a contact means for controlling the measuring operation.

2. A measuring device in accordance with claim 1, wherein the contact means is a button that can be actuated by a user.

3. A measuring device in accordance with claim 1, further comprising a device housing with a device door which separates the measuring device from the environment.

4. A measuring device in accordance with claim 1, wherein the contact means is provided for monitoring the status of the device.

5. A measuring device in accordance with claim 4, wherein the contact means is a switching contact actuated by a contact maker located on the device door.

6. A measuring device in accordance with claim 4, wherein the contact means is a switching contact actuated by a contact maker located at the test sample holder.

7. A measuring device in accordance with claim 4, wherein the contact means is a switching contact actuated by a contact maker located at the fluid tank.

8. A measuring device in accordance with claim 4, wherein the test sample holder comprises a contact maker of said contact means.

9. A measuring device in accordance with claim 4, wherein the fluid tank comprises a contact maker of said contact means.

10. A measuring device in accordance with claim 4, wherein said contact means comprises contact elements with one of said contact elements comprising a photoelectric cell.

11. A measuring device in accordance with claim 4, wherein the contact means comprises contact elements including an electromechanical contact actuated by an external magnetic field effect and a contact maker made of a magnetic material and generating a magnetic field to bring about an actuation of the contact element when approaching said contact element.

12. A measuring device in accordance with claim 1, wherein said test sample holder is provided with a code.

13. A measuring device in accordance with claim 1, wherein said optical reading element comprises means for reading a code at said test sample holder and wherein said optical analysis unit is designed to analyze the code.

14. A measuring device in accordance with claim 1, wherein the heating/cooling element comprises a separate heating element and as a separate cooling element, which are arranged together at said tempering block and are actuated by said temperature regulating unit.

15. A measuring device in accordance with claim 1, further comprising an additional heating element.

16. A measuring device in accordance with claim 1, further comprising an electric energy storage unit connected to said temperature regulating unit.

17. A measuring device in accordance with claim 1, wherein:
values of the ambient temperature are entered in a specification column in said control chart with a first value block provided for a first phase, comprising a first set of temperature values and a first set of time period values, and with a second value block provided for a second phase, comprising a second set of temperature values and a second set of time period values;
a code of the test sample holder and the ambient temperature and the temperature of the tempering block and the first and at least one second value block are used as controlled variables for said temperature regulating unit for regulating the temperature of said tempering block and for said metering unit for metering said developer fluid onto a test strip.

18. A measuring device in accordance with claim 17, further comprising a data interface wherein a refreshing of the data of the control chart by means of data transmission via said data interface is provided.

19. A measuring device in accordance with claim 1, wherein the optical reading element is for reading a color change on a test strip in said test sample holder and wherein said optical analysis unit is designed to analyze the color change.

20. A measuring device for measuring a test sample in a test sample holder, the device comprising:
a housing;
a tempering zone arranged in said housing, said tempering zone being receivable of the test sample holder, said tempering zone being capable of adjusting a temperature of the test sample holder when the test sample holder is in said tempering zone;
a fluid tank arranged in said housing to flow a developer fluid to the test sample holder, when the test sample holder is in said tempering zone;
an optical analysis unit arranged in said housing, said optical analysis unit including an optical reading element arranged to read the test sample holder when the test sample holder is in said tempering zone, said optical analysis unit measuring details of the test sample in the test sample holder;
a first temperature sensor connected to said housing and measuring an ambient temperature of air inside said housing;
a second temperature sensor connected to said housing and measuring a temperature of said tempering zone which adjusts the temperature of the test sample holder;
a control unit connected to said tempering zone, connected to said first temperature sensor and connected to said second temperature sensor, said control unit selectively setting a temperature of said tempering zone based on the ambient temperature.

21. A measuring device in accordance with claim 20, wherein:
said tempering zone selectively heats and cools the test sample holder according to commands from said control unit.

22. A measuring device in accordance with claim 20, wherein:
said control unit selectively sets the temperature of said tempering zone in a first phase and a second phase, said first phase having a first temperature and a first time interval, said second phase having a second temperature and a second time interval.

23. A measuring device in accordance with claim 22, wherein:
values of said first temperature, said second temperature, said first time interval and said second time interval are selectively set by said control unit dependent on the ambient temperature measured by said first temperature sensor.

24. A measuring device in accordance with claim 23, further comprising:
a temperature control chart connected to said control unit and providing said values of said first temperature, said second temperature, said first time interval and said second time interval dependent on the ambient temperature measured by said first temperature sensor, said first temperature and said second temperature being different for one of the ambient temperatures.

25. A measuring device in accordance with claim 20, further comprising:
a code reader connected to said housing and readable of a code on the test sample holder;

said control unit receiving the code from said code reader, said control unit selectively setting the temperature of said tempering zone based on the ambient temperature and the code read from the test sample holder by said code reader.

26. A measuring device in accordance with claim 22, further comprising:
a code reader connected to said housing and reading a code on the test sample holder;
a temperature control chart connected to said control unit and providing values for said first temperature, said second temperature, said first time interval and said second time interval dependent on the ambient temperature measured by said first temperature sensor and the code read from the test sample holder;
said control unit receiving the code from said code reader, said control unit selectively setting the temperature of said tempering zone based on said temperature control chart, the ambient temperature and the code read from the test sample holder.

27. A measuring device in accordance with claim 25, wherein:
said control unit controls a set temperature of said tempering block using said second temperature sensor;
said optical analysis unit is also said code reader.

28. A measuring device in accordance with claim 20, wherein:
said control unit selectively sets a temperature of said tempering zone in a first phase and a second phase, said first phase having a first temperature and a first time interval, said second phase having a second temperature and a second time interval;
said control unit is also connected to said fluid tank and controls said fluid tank to selectively flow the developer fluid to the test sample holder, said control unit flowing the developer fluid to the test sample holder between said first phase and said second phase.

29. A process for operating a measuring device comprising an electronic unit including a central control unit, a sequential control and a control chart, an optical analysis unit with an optical reading element, a metering unit, a fluid tank containing a developer fluid, a holder for the fluid tank, a temperature regulating unit, a test sample holder, a heating/cooling element with a tempering block for generating a tempered zone of the test sample holder, temperature sensors for detecting the ambient temperature and the temperature of the tempering block and a contact means for controlling the measuring operation, the process comprising the steps of:
transferring a section of a process control from the central control unit to the sequential control and to the temperature regulating unit;
polling first and second of the temperature sensors and preparing the temperature regulating unit;
inserting the test sample holder into the measuring device;
closing the measuring device by closing a measuring device housing door;
polling one or more contact elements;
polling a code on the test sample holder;
using the control chart, the code and the measured values of the temperature sensors to determine control parameters for tempering;
tempering of the tempering block and setting the temperature of the tempering block by the temperature regulating unit based on the ambient temperature;
metering the developer fluid onto a sample by means of the metering unit;
additional tempering of the tempering block and setting of the temperature of the tempering block by the temperature regulating unit is performed after said metering;
ending tempering; and
transferring the process control to the central control unit.

30. A process in accordance with claim 29, further comprising feeding of a defined quantity of the developer fluid from a storage tank in an interior space of the measuring device to the metering unit.

31. A process in accordance with claim 29, wherein pre-tempering of the tempering block is carried out during or soon before or soon after said step of polling the first and second temperature sensors.

32. A process in accordance with claim 29, further comprising:
maintaining a set temperature of said tempering block using the detected temperature of the tempering block and according to a proportional-integral control characteristic.

* * * * *